United States Patent [19]

Shanks et al.

[11] Patent Number: 4,457,305
[45] Date of Patent: Jul. 3, 1984

[54] WATER TRAP ASSEMBLY

[75] Inventors: Thomas P. Shanks, Temecula; Robert P. Price, San Diego, both of Calif.

[73] Assignee: Hudson Oxygen Therapy Sales Company, Temecula, Calif.

[21] Appl. No.: 401,958

[22] Filed: Jul. 26, 1982

[51] Int. Cl.³ .......................................... A61M 16/00
[52] U.S. Cl. .............................. 128/205.12; 55/461; 55/466; 55/DIG. 35; 128/205.27
[58] Field of Search ............... 128/206.22, 203.16, 128/203.19, 203.12, 204.25, 205.12, 205.27; 55/466, 524, DIG. 35, 429, 461, 164, 185, 192, 159; 137/402

[56] References Cited

U.S. PATENT DOCUMENTS

| | | | |
|---|---|---|---|
| 3,454,005 | 7/1969 | Eubanks et al. | 128/205.12 |
| 3,682,166 | 8/1972 | Jacobs | 128/205.12 |
| 4,020,834 | 5/1977 | Bird | 128/205.12 |
| 4,090,513 | 5/1978 | Togawa | 128/205.12 |
| 4,327,718 | 5/1982 | Cronenberg | 128/205.12 |

Primary Examiner—Henry J. Recla
Assistant Examiner—Karin M. Reichle
Attorney, Agent, or Firm—Seiler, Quirk & Tratos

[57] ABSTRACT

An assembly for collecting condensed water vapor or moisture in a breathing circuit comprises a lid having an inlet and an outlet pipe connected to the breathing circuit, a jar removably secured to the lid, a drain funnel having a port at the bottom for directing water into the jar, and a movable seal in the funnel for being biased gravitationally to occlude the port and form a gas tight seal with the port when the jar is removed from the lid.

3 Claims, 2 Drawing Figures

WATER TRAP ASSEMBLY

BACKGROUND OF THE INVENTION

In breathing circuits for administering respiratory therapy to patients, oxygen enriched gas combined with an aerosol is commonly used. Volume ventilator circuits normally incorporate a nebulizer as do IPPB systems or circuits. In any of these or similar systems for administering respiratory therapy, flexible corrugated tubing is normally used, often of substantial length, for example at least three feet, and commonly up to five feet, between the patient and the gas source. Because of the presence of the aerosol or highly humidified gas in the long length of tubing, condensation of water vapor and moisture occurs along the tubing and collects at any low points or bends. Where therapy is prolonged, substantial water can accumulate, which is undesirable.

Water traps or collectors for condensed water vapor and moisture in respiratory and ventilator system tubing have been used heretofore. However, such device have included spring biased valves for maintaining a gas-tight seal when the water collecting jar or container is removed from the system. Although such devices are initially efficient, springs are expensive and often take a set or otherwise deteriorate, so that they have not been entirely satisfactory, especially when used over a period of time. Moreover, non-uniformity of the springs results in non-uniform sealing for a given product line.

SUMMARY OF THE INVENTION

It is to an improved water trap and collection system in a respiratory therapy breathing circuit that the present invention is directed. The device uses no springs or other similar biasing means, but instead forms a gas-tight seal incorporating a gravitationally biased sealing means. The advantages of such a device will be evident from the following detailed description.

DETAILED DESCRIPTION OF THE INVENTION

Figure 1:
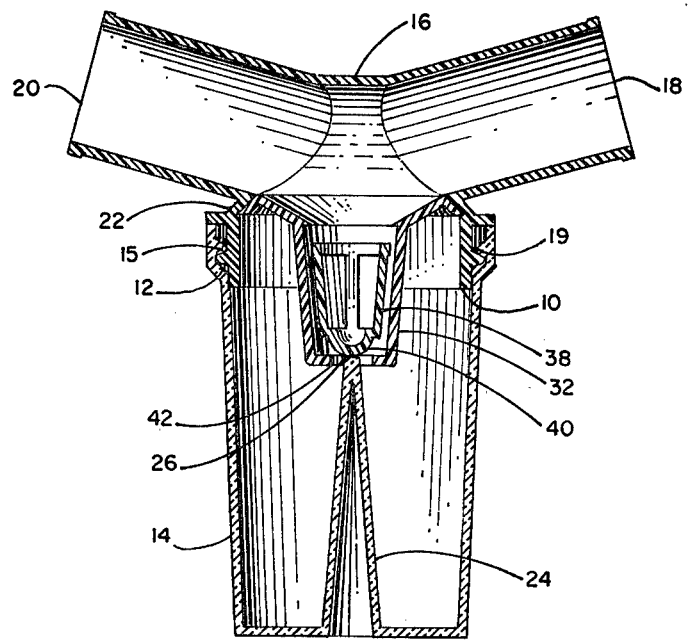
FIG. 1 is a side sectional elevation illustrating the components of the moisture collecting assembly of the invention.

As shown in FIG. 1, the improved assembly includes a lid 16 having inlet and outlet pipes 18 and 20, respectively. These pipes, which are simply hollow conduits, are of a size for being directly connected to a standard 22 mm corrugated tubing ends or adapters. For this purpose, the pipes may be slightly tapered along their respective lengths to insure a snug fit with the tubing, or adapter. The pipes are slanted downwardly along their respective lengths, at least slightly, from the outer ends toward the center of the lid. The lid includes a downwardly extending annular skirt 22 having threads 19 formed on the outer surface for engaging threads at the jar which is removably secured on the skirt.

A second component of the assembly is jar 14 into which moisture is collected. In the preferred embodiment shown, the jar includes a protruding member 24, molded integrally as a portion of the jar, which extends upwardly sufficiently to contact sealing member 38 when the jar is secured to the lid 16. The jar also includes threads 15 for engaging threads 19 of the lid.

Another important feature of the assembly is that when the jar is fully secured on the lid, a gas-tight seal is formed therebetween so that there is no interference with the efficiency of the gas delivery apparatus in which the assembly is used. For this purpose, in the embodiment shown, bottom edge 10 of skirt 22 engages slanted shoulder 12 of jar 14 to form a gas-tight seal therebetween when the latter is fully secured on the lid. Other alternative locations or means for achieving the gas-tight seal between the jar and lid may also be used.

Figure 2:
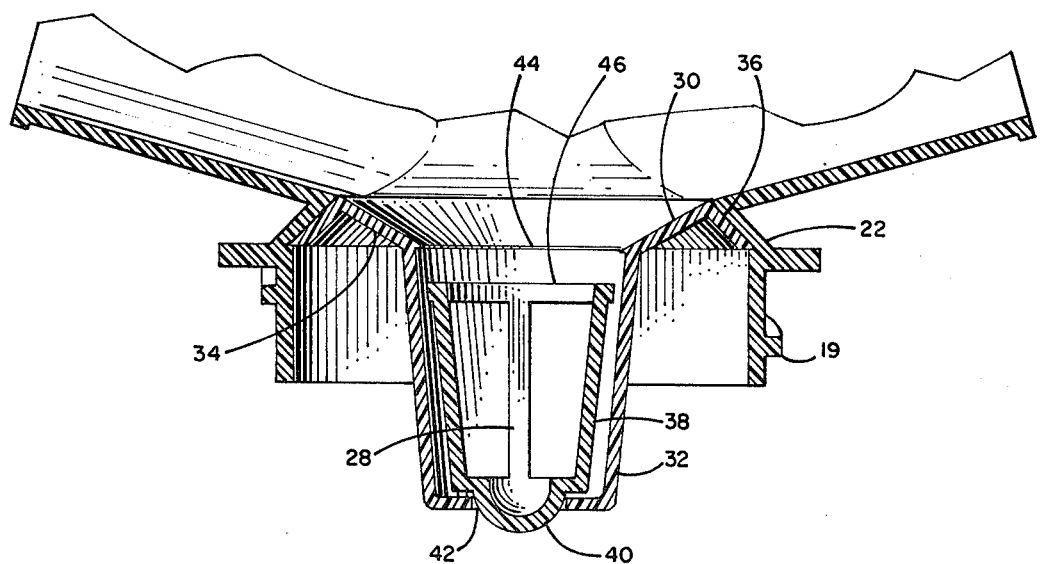
FIG. 2 is an enlarged view of the drain and gravitationally biased seal member of the assembly.

Referring also to FIG. 2, there is illustrated the moisture drain components of the invention including drain member 30 having downwardly extending funnel 32 and bottom port 42. The drain member may be simply an integral portion of lid 16, but, preferably it is a removable component. As such, with the two components separately formed, they are less expensive to mold, and assembly is improved with the insertion of the sealing member in the funnel. The drain member 30, is removably secured to the inside or interior surface of skirt 22 and forms a gas-tight seal therewith. In the embodiment shown, pan 34 which is slanted downwardly for drainage of water into funnel 32, includes a cuff 36 which is slightly oversized relative to the interior surface diameter of the skirt. The cuff is flexible so that it can be force fitted into the skirt to form the necessary gas-tight seal. It will be evident that due to the funnel shape of drain member 30 including the downwardly inclined pan surface 40 and funnel 32, water from condensed water vapor passing into the lid will be directed outwardly into the funnel and to bottom port 42 thereof.

Within main member 30 is a sealing member 38 having means for forming a gas-tight seal with port 42. In the embodiment shown, sealing member 38 includes a plug 40, that shown being a spherical shape, although any other suitable plug shape may be used, for forming a gas-tight seal with the surface of port 42. Accordingly, plug 40 must be of a shape so that when it rests in the port, it will form the required gas seal. The other features of the sealing member include a plurality of ribs 28 which provide openings through which water can pass. Moreover, in the preferred embodiment, the sealing member includes an enlarged body portion 46 which cannot be easily dislodged from the interior of funnel 32. Thus, a restricting surface 44 being somewhat smaller than the size of the body portion 46 will be suitable, and prevent the sealing member from inadvertently being removed or falling out of the funnel when the assembly is on its side or even upside down. Any other suitable means to provide for this advantage may be used.

In operation, with the jar 14 fully secured on lid 16, end 26 of projecting member 24 contacts plug 40 and pushes it upwardly whereby port 42 is open. When installed in a respiratory therapy circuit or system, with the assembly secured along a length of tubing, condensed water vapor is directed along the pipes, the drain member, and into the jar through port 42. When sufficient water has collected in the jar so that it should be emptied, the jar is simply unscrewed from the lid. Due to the initial gas leak at port 32 and the pressure drop caused by the open port between ambient and the gas pressure in the circuit, sealing member 38 is forced to occlude the opening. The member is also gravitationally biased so that plug 40 tends to occlude port 42 because of the disengagement of the plug with the projecting member 24. Since a gas-tight seal is formed by the plug at the port, there is no significant interruption of gas delivery in the breathing circuit, and efficiency is not interrupted or altered. Once the jar has been emptied, it is simply again secured to the lid, whereby plug 40 is moved to again open port 42 for repeating the water collection process. These as well as other advantages of the assembly and modifications within the purview of the invention will be evident to those skilled in the art.

I claim:

1. An assembly for collecting condensed water vapor and moisture from a gas directing tube comprising:
    a lid member having an inlet pipe and an outlet pipe for being connected to said tube,
    a removable jar releasably mounted on said lid member for collecting said condensed water vapor and forming a gas-tight seal with said lid member,
    a drain member secured in said lid member having a funnel portion with a port at the bottom thereof for directing condensed water vapor from said lid member to said jar, and
    a movable seal member in said funnel portion gravitationally biased to occlude said port and to form a gas-tight seal thereat when said jar is removed from said lid member, wherein said jar further includes means for moving said seal member from sealing engagement with said port when said jar is secured on said lid member.

2. The assembly of claim 1 wherein said means for moving said seal member comprises a projecting member for engaging said seal member and holding it away from sealing engagement with said port.

3. The assembly of claim 1 wherein said drain member forms a releasable gas-tight seal with said lid.

* * * * *